United States Patent [19]

Gorman

[11] Patent Number: 5,400,794
[45] Date of Patent: Mar. 28, 1995

[54] BIOMEDICAL RESPONSE MONITOR AND TECHNIQUE USING ERROR CORRECTION

[76] Inventor: Peter G. Gorman, Lakeview Dr., Mahopac, N.Y. 10541

[21] Appl. No.: 33,826

[22] Filed: Mar. 19, 1993

[51] Int. Cl.⁶ .......................................... A61B 5/0428
[52] U.S. Cl. ...................................... 128/696; 128/903
[58] Field of Search ......................... 128/696, 706, 903

[56] References Cited

U.S. PATENT DOCUMENTS

| | | | |
|---|---|---|---|
| 3,212,496 | 10/1965 | Preston | 128/206 |
| 3,724,455 | 4/1973 | Unger | 128/2.06 |
| 3,949,388 | 4/1976 | Fuller | 340/189 |
| 3,972,320 | 8/1976 | Kalman | 128/2.1 A |
| 3,986,498 | 10/1976 | Lewis | 128/2.06 R |
| 4,425,921 | 1/1984 | Fujisaki et al. | 128/690 |
| 4,478,224 | 10/1984 | Bailey | 128/706 |
| 4,625,733 | 12/1986 | Saynajakangas | 128/687 |
| 5,117,825 | 6/1992 | Grevious | 128/903 |
| 5,157,604 | 10/1992 | Axford et al. | 364/413 |

Primary Examiner—William E. Kamm

[57] ABSTRACT

A monitor for measuring and displaying a biomedical response such as heartbeat rate, including a transmitting unit and a receiving unit. The monitor detects the response (heartbeat) and produces a digital pulse train representing this response. The digital pulse train is then encoded to produce an encoded digital signal having a first identification part identifying the transmitting unit and a second data part representing the person's response. This encoded digital signal is wirelessly sent to the receiving unit which reads the received signal to determine if it is from the transmitting unit. If it is from that transmitting unit, the data part is read. If there are too many errors in the data part, a new frequency of wireless transmission is used in the monitor. If the errors are within a reasonable bound, the data bits representing the biomedical response are sent to a memory and/or a display. If the received signal were not from the correct transmitting unit, the received signal is rejected. Interference from other monitors or electrical equipment is minimized, and the data displayed is very accurate.

45 Claims, 5 Drawing Sheets

FIG. 1
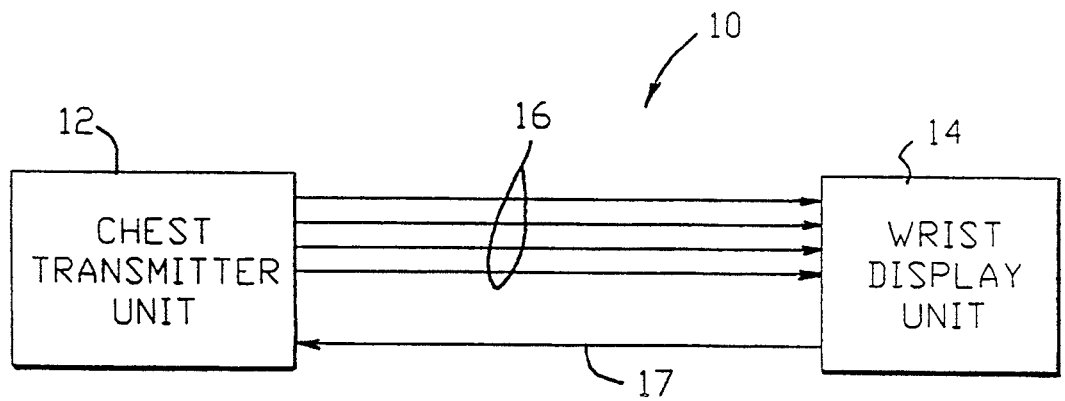
FIG. 2
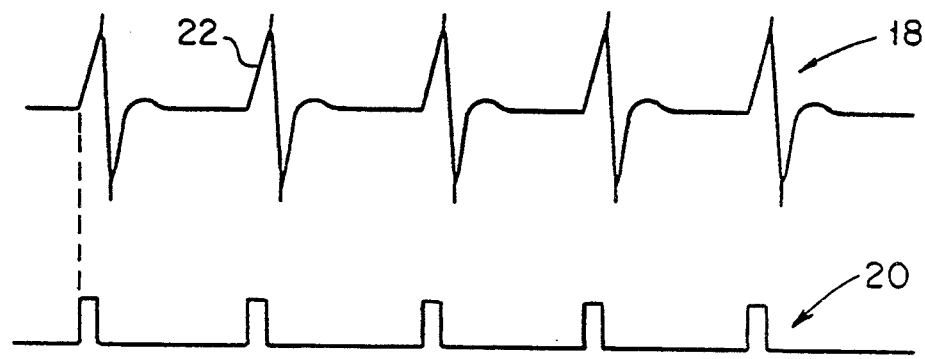
FIG. 3A
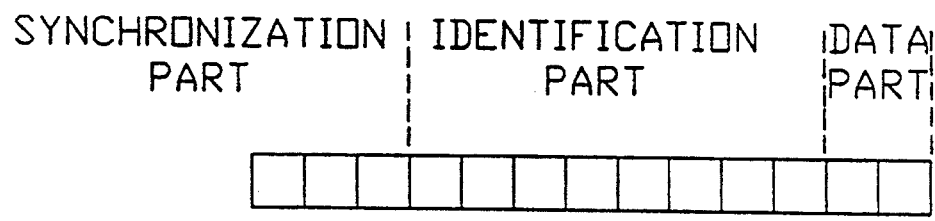
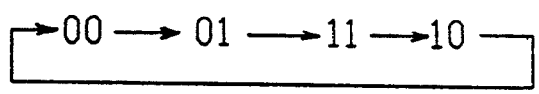
FIG. 3B

TRANSMITTER UNIT

BIOMEDICAL RESPONSE MONITOR AND TECHNIQUE USING ERROR CORRECTION

DESCRIPTION

Field of the Invention

This invention relates to a technique and apparatus for wirelessly monitoring a physical condition or body response such as heartbeat, and more particularly to such a technique and apparatus in which errors due to interfering sources are minimized or eliminated and in which improved accuracy results due to error detection and correction in the pattern representing the body response.

Background Art

For many applications, it is necessary to measure and display a person's body response, such as his or her heartbeat. In particular, in exercise and fitness training, it is often the situation that a person wishes to measure his or her heartbeat in order to achieve the maximum benefits of the exercise without the danger of increasing the heartbeat to a rate where adverse effects could occur. Of course, such measurements are also useful for many health applications such as biofeedback and exercise programs where the participants only mildly exercise and do not approach greatly elevated heart rates. Over the years, various types of equipment have been marketed for the measurement of heart rate, such instruments being popular in a wide variety of applications extending from all forms of exercise to biofeedback. Continuous accurate heart measurement is an important part of all aerobic exercise and rehabilitation programs and for this reason many types of apparatus have been commercially available for personal use by individuals and in fitness clubs, etc.

Some of the most popular heartbeat monitor designs use wireless data transmission from a sensor-transmitter unit to a display unit. This type of design allows optimal and flexible positioning of both units while not limiting a person's freedom of movement. Unfortunately, the increasing popularity of heart measurement, and therefore the use of these heart monitors, has demonstrated the limitations of currently available designs. An example is the recurring interference effects brought about when a person wearing a heart monitor is in close proximity to another person wearing another heart monitor. These people run the risk that their individual monitor readings are influenced by the monitor worn by the other person. Further, it is equally frustrating for a person wearing a heart monitor to find that electromagnetic equipment of all types, such as exercise equipment, power lines etc. will create electromagnetic fields that interfere with the successful transmission of his or her heartbeat, thereby causing an erratic display which is uncorrectable without moving away from the interfering exercise equipment, power lines, etc.

Various types of wireless measuring methods have been proposed. Some of these are based on radio waves while others use a magnetic proximity field. Most of these prior techniques transmit an analog ECG signal of a person. However, as noted, these prior techniques and apparatus are not simultaneously usable by several persons in close proximity to one another or by persons who are using such apparatus in close proximity to electrical or electronic equipment. In such cases, the reliability of transmission of heartbeat is significantly reduced with the result that a continuous and accurate monitoring of the heartbeat is no longer possible. As is readily appreciated, this lack of reliability is a problem for anyone using the monitor and is especially disconcerting to a person who is exercising to a level where his or her heartbeat is close to the maximum desired for that person.

Examples of some prior art monitors include U.S. Pat. No. 4,625,733; U.S. Pat. No. 4,425,921; U.S. Pat. No. 3,212,496; and U.S. Pat. No. 3,949,388. The first of these describes a heartbeat monitor using a magnetic proximity field as a basis for analog wireless transmission, where a particular arrangement of magnetic coils is used in the transmitter and the receiver units.

U.S. Pat. No. 4,425,921 describes a portable heartbeat monitor which can be used to check either pulse rate or heart rate using separate sensors for detecting heartbeat and pulse beat. The apparatus shares a common indicator for displaying the heartbeat rate or pulse beat rate depending upon a switch means for connecting either of the sensors to a microcomputer. Analog signals are used in this monitor, which does not use wireless transmission between a transmitter and receiver.

U.S. Pat. No. 3,212,496 describes an apparatus for simultaneously measuring ECG, respiration rate, and respiration volume. A pair of electrodes on or in a person's body have current passed therebetween and sense an impedance change and a heartbeat voltage. A frequency modulated signal can then be telemetered to a receiving and display unit.

U.S. Pat. No. 3,949,388 describes a portable apparatus that can be used for analog biomedical telemetry, and is particularly adapted for use in a hospital where each sensor-transmitter unit is used on a single patient and will not normally be used on another patient. The transmitter is designed to produce a very narrow frequency spectrum where a steady pulse rate accurately represents the measured temperature of the patient. In order to avoid interference from adjacent units, the receiver unit is located within only a few feet of the transmitting unit. Further, a very low power continuously sending transmitting unit is used so that only the closest receiver will detect the analog signal. This avoids the possibility that the receiver will pick up signals from another transmitter. Thus, the selectivity of the receiver is based on its close proximity to the associated transmitter unit not on any circuitry which would prevent interference by a transmitter broadcasting a high power signal, even though such interfering transmitter may be far away. Further, the frequency range intended for operation is selected to be very narrow. As noted in this patent, frequency sweeping can occur due to saturation of a transistor in the oscillator circuit. In order to prevent this undesirable frequency sweeping, an isolating impedance is used in the circuit design to prevent feedback current of the type which causes the transistor saturation.

U.S. Pat. No. 5,157,604 describes a hospital monitoring system in which many patient transmitter units are coupled to a central station. Wireless transmission of a signal including an identifier and heartbeat data occurs from each patient unit to the central station. Each patient unit transmits on its own frequency so there will be not interference between the patient units. The responses of the patient units are time multiplexed, since these units respond to the central station only in response to the receipt of a timing signal from the central station. Error detection and correction of an incorrect heartbeat due to faulty transmission is not mentioned.

In the prior art monitors for measuring and displaying heartbeat, it is usually not possible to provide a technique and apparatus for determining if the received signal in the display unit is from the properly associated transmitter unit or is instead from another transmitter unit. Further, if there are errors occurring in the data representing the heartbeat, such as missing portions of the signal due to interference from outside sources, the display in these prior monitors will either indicate a wrong value, not indicate heartbeat, or maintain the previous reading without making the user aware of the problem. Further, in these prior art monitors, there is no way to account for transient errors in heartbeat which are momentarily caused but which do not necessarily render inaccurate the later readings of heartbeat.

It is therefore a primary object of the present invention to provide an improved technique and apparatus for monitoring and displaying a biomedical function (body response) such as heartbeat, wherein the above-described problems are addressed and corrected.

It is another object of the present invention to provide an improved personal use heartbeat monitor which automatically rejects interfering signals from sensor-transmitter units other than the one with which the display unit is properly associated.

It is another object of the present invention to provide a heartbeat monitor in which the presence of transient errors in the signal representing the heartbeat do not render inaccurate the heartbeat displayed to the person wearing the monitor.

It is another object of this invention to provide a wireless heartbeat monitor which can be easily worn by a person engaged in all forms of physical exercise, and which will nonetheless provide accurate measurement of the person's heartbeat even in the presence of other heartbeat monitors and/or electrical or electronic equipment.

It is another object of the present invention to provide an improved heartbeat monitor in which a part of a person's ECG signal is digitally encoded for wireless transmission to a receiver-display unit, where the coding allows a receiver-display unit to identify the encoded digital signal as having been sent from a particular sensor-transmitter unit.

It is another object of the present invention to provide a heartbeat monitor which will automatically change the frequency range over which signals representing the heartbeat are wirelessly sent from a sensor-transmitter unit to a receiver-display unit, the transmission frequency being changed in response to the occurrence of errors in the received signal.

It is another object of this invention to provide an improved wireless heartbeat monitor wherein signal encoding is utilized to provide unique identification between a sensor-transmitter unit and a receiver-display unit.

It is another object of this invention to provide an improved heartbeat monitor and technique in which non-repetitive errors in the signal wirelessly transmitted from the sensor-transmitter unit to the receiver-display unit do not affect the accuracy of the heartbeat displayed to the person wearing the monitor.

It is a further object of this invention to provide a technique and apparatus for monitoring heartbeat where the monitor can be used in various environments, including in the presence of exercise equipment, electronic equipment or electrical equipment, without adversely affecting the accuracy of the data displayed to the person using the monitor.

It is another object of this invention to provide an improved technique for isolating monitor signals relating to a biological function, such as heartbeat, wherein the monitored signals are digitally encoded to provide user identifiers that are wirelessly transmitted.

It is a still further object of this invention to provide automatic transmission error detection and correction in a wireless biological response monitoring system.

BRIEF SUMMARY OF THE INVENTION

This invention broadly relates to an improved technique and apparatus for measuring and displaying, preferably on a continuous basis, a physical condition or biomedical response, such as a heartbeat rate. The apparatus includes a transmitter unit for producing an encoded digital signal representing the biomedical response and for wirelessly transmitting the encoded digital signal to a receiver unit for display of the measured biomedical response. The monitor also includes a detection means for detecting errors in the received encoded digital signal, and correction means for automatically changing the transmitter unit and the receiver unit to provide accurate wireless transmission therebetween of the measured biomedical response. In a preferred embodiment this monitor includes unique identification between a transmitter and an associated receiver.

This monitor is particularly suitable for personal use such as would occur in a home or office or even in a gym or fitness center. In one embodiment, the transmitter and receiver units are adapted to be worn and would be battery operated. As an alternative, the receiver unit can be part of exercise equipment or a small portable unit that can be free standing. As long as the receiver is within the transmission distance from the transmitter, it will receive the wirelessly transmitted signal. In one aspect of this invention an apparatus and technique are described for monitoring a person's heartbeat and for displaying an indication of the mentioned heartbeat. In a preferred embodiment, the apparatus is comprised of a sensor-transmitter unit (chest unit) adapted to be worn in contact with a person's chest and having electrodes which receive the person's ECG signal. This signal is amplified and digitally encoded to contain an identification portion and a data portion. This encoded signal is transmitted in a wireless manner to a receiver-display unit (wrist unit), where the wrist unit contains a display for displaying the person's heartbeat. While the display portion of the monitor is preferably adapted to be worn, for exp. on a person's wrist, this unit need not be worn and could be located elsewhere, for example on exercise equipment. Further, while chest electrodes generally provide the best ECG signals, the transmitter unit could be placed elsewhere, such as on a person's wrist.

Because the person's ECG signal is digitized and encoded, two purposes can be achieved. The first is that an identification is provided which is different for each heart monitor. That is, after the wrist unit receives the transmitted encoded signal, it checks this signal to see if it contains the proper identification code. If this comparison fails, the incoming signal to the wrist unit is not accepted because it is not from the proper chest unit. However, if the identification compares with the reference identification in the wrist unit, the incoming signal will be accepted. This prevents two heart monitors working in close proximity to each other and transmitting on the same frequency from receiving and displaying signals from the wrong person.

The second purpose of the digital encoding is to provide transmission error detection and correction of the heartbeat data. In practice, it is possible that a valid signal may be rejected by the wrist unit due to an outside noise source. The data portion of the transmitted signal is therefore encoded into a particular bit sequence. When the incoming data bit sequence is checked against a reference data bit sequence in the wrist unit, errors in the received signal can be detected. The wrist unit can be set so that infrequently occurring errors (such as transient errors) will be corrected but not result in a change of the transmitting and receiving units. On the other hand, if too many errors are present, the wrist unit will notice it and provide a frequency change signal to change the transmission frequency in the chest unit and also to change the receiving frequency in the wrist unit. In a preferred embodiment the power of the frequency change signal is also increased to ensure that the frequency change is made. While the wrist unit will automatically cause a change in frequency if persistent errors occur, the user can also change the transmission and reception frequency if it is anticipated that a problem may occur. This feature of a change in transmission and receiving frequency also allows the use of multiple units in close proximity to one another without reciprocal disturbances.

The chest unit generally contains an input sensor means for receiving the ECG signal, amplifying means, comparator means for producing a digital pulse train corresponding to the analog ECG pulses, encoder means for encoding the digital pulse train into coded signals having bits corresponding to an identification portion and further bits corresponding to a data portion of said encoded signal, and means to receive a frequency change signal from the wrist unit for changing the transmitting frequency of the chest unit. This latter means includes a receiver for receiving via wireless transmission the frequency change signal from the wrist unit when the transmission frequency is to be changed and a signal evaluator for reading the identification code in the frequency change signal to determine that it is from the associated wrist unit and for providing a signal to the transmitter means for changing the transmission frequency for the outgoing signals from the chest unit. Part of the identification signal may serve for synchronization of a clock signal in the wrist and chest units.

The wrist unit broadly includes a receiver for receiving output signals from the chest unit and a signal evaluator for separating the identification portion and the data portion of the incoming encoded signal and for determining if the incoming signal is from the associated chest unit. The signal evaluator also checks the data portion of the incoming signal to determine if its has the proper data pattern for the associated chest unit. The signal evaluator provides an output to memory means for storing heartbeat data and also provides an output that is sent to a display, for displaying the heartbeat rate. The signal evaluator further provides an output that is sent to a transmitter means located in the wrist unit if the signal evaluator determines that the frequency of errors in the data portion of the incoming signal is beyond a given bound, that is, if the bit patterns indicate that the errors are not merely transient but are sufficiently repetitive as to provide potentially inaccurate monitoring of person's heartbeat. The output of the transmitter means in the wrist unit is sent in a wireless manner to the receiver in the chest unit. At the same time, the signal evaluator also provides a signal to the receiver in the wrist unit to change its reception frequency to match the new transmission frequency in the chest unit. The wrist unit also contains an input terminal by which the user can directly initiate a change in transmitter/receiver frequency, or can block an automatic change of frequency in the chest and wrist units. For example, the user may sense that the external condition which is causing an error in the received encoded signal will soon cease so that it is not necessary to change frequency. Another situation where a user may want to prevent a frequency change is where there are multiple users in close proximity. Rather than have everyone's monitor change frequency, some monitors can be held at fixed frequencies while other monitors change frequency.

The design will overcome most of the limitations of the currently available wireless heart monitors. Additionally, it will compensate for minor errors and enable the user to avoid certain error sources by purposely changing the transmission frequency. Of course, the user can allow the monitor to automatically change frequencies. Since the range of the human heart rate is fairly restricted, this design allows the detection of uncorrectable errors by taking into account the elapsed time between two successful data transmissions. Since it is highly improbable that the wrist unit will receive the correct identification pattern from a source other than the associated chest unit, the user can have a very high level of confidence in the accuracy of the displayed heart rate. This is accomplished even though the chest and wrist units are separate from one another and communication therebetween is via wireless transmission.

The invention is most useful in the case of personal use equipment which allows the user to have complete mobility while undergoing heartbeat monitoring. The various components of the chest and wrist units are easily provided by known microelectronic integrated circuit chips that can be packaged together in small volume and battery operated. The major use of this monitor will be for continuous display during personal activities by an individual, including exercise, biofeedback, and general health monitoring. In these activities wireless transmission will be over a relatively short range, particularly if both the transmitter and receiver units are worn.

These and other objects, features, and advantages will be apparent from the following more particular description of the preferred embodiments.

BRIEF DESCRIPTION OF THE DRAWINGS

FIG. 1 is a schematic illustration of the heart rate monitor of the present invention, showing the chest unit (transmitting unit) and the wrist unit (display) which receives the signal from the chest unit via a wireless transmission and displays the heartbeat of the person being monitored.

FIG. 2 shows a typical ECG signal and the train of digital pulses representing each of the analog pulses in the ECG signal.

FIG. 3A shows a typical format of the encoded digital signal wirelessly transmitted from the chest unit to the wrist unit, this digital signal consisting of a synchronization part, an identification part unique to this particular chest monitor and a data part unique to the person's heartbeat.

FIG. 3B represents a sequence of bits corresponding to the data part of the outgoing digital signal from the unit (FIG. 1) where each data part is represented as a two-bit binary code in this example.

DETAILED DESCRIPTION OF THE PREFERRED EMBODIMENTS

Figure 4:
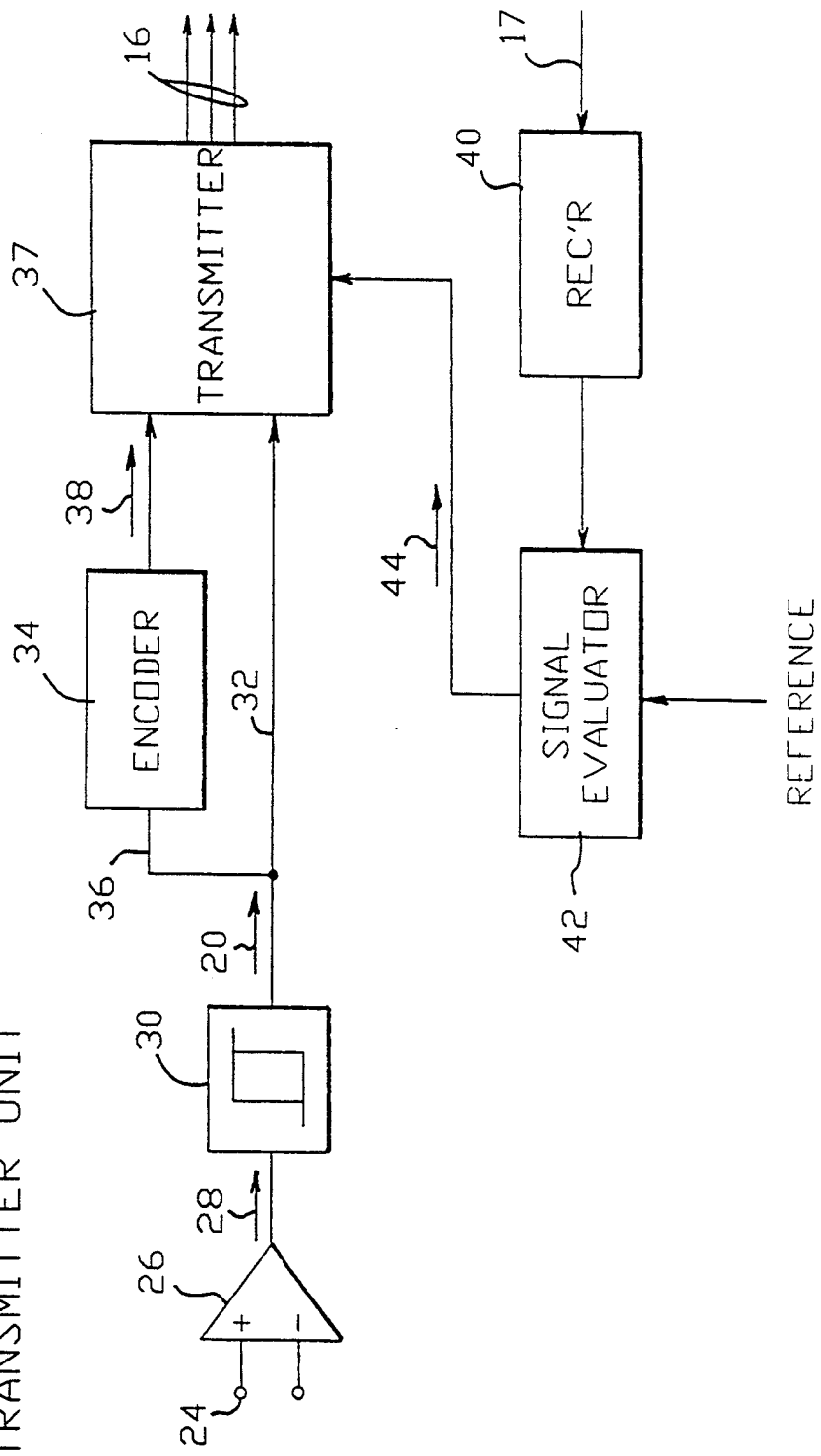
FIG. 4 is a schematic illustration of the chest unit in more detail, showing the various components of this unit.

The practice of this invention will be represented by the example of a heartbeat monitor, where it is desired to accurately measure heartbeat and to provide a technique which eliminates many of the errors found in the use of presently available wireless heartbeat monitors, particularly those of the portable type adapted to be used by people undergoing exercise, biofeedback etc. Such problems generally relate to interference effects that can occur if two wireless heartbeat monitors are operating in close proximity to one another, noise attributable to sources other than another heart monitor, confusion between received signals wherein the heartbeat being displayed may not be that of the person being monitored and situations where the user would be unaware that the displayed heartbeat is inaccurate.

FIG. 1 schematically represents the heartbeat monitor 10, which is comprised of a chest unit 12 (transmitting unit) and a complementary wrist unit 14 (receiving or display unit). Wireless transmission over a plurality of frequency ranges can occur from chest unit 12 to wrist unit 14, as represented by the arrows 16. Wireless transmission from the wrist unit 14 to the chest unit 12 is used to correct transmission errors but usually over only a single frequency as represented by the single arrow 17. As will be described later, wireless transmission from the display unit 14 to the chest unit 12 will occur when it is desired to change the transmission frequency from the chest unit. This can be done either automatically or on command by the user. In practice, the transmitter of the chest unit is frequency matched to the receiver in the wrist unit so that an encoded digital signal wirelessly transmitted from the chest unit 12 will be correctly received by the wrist unit 14.

FIG. 2 illustrates a typical ECG signal 18 from a person being monitored, and the digital pulse train 20 corresponding to the ECG signal. Each digital pulse corresponds to the onset of a positive slope portion 22 of the analog pulses forming the ECG signal train 18. As an alternative, each digital pulse can correspond to another portion of the analog pulses, such as the peak of each pulse. In the present invention, the ECG signal is digitized prior to wireless transmission from the chest unit 12 to the wrist unit 14. The purpose of this apparatus is to monitoring heartbeat and therefore it is sufficient to transform the ECG signal into a digital pulse train. The particular characteristics relating to a person's ECG signal are not of importance in the present invention.

Prior to the transmission of a digital signal from chest unit 12 to wrist unit 14, the digital signal is given a specific binary identification sequence. Further, the individual digital pulses in the pulse train 20 are each encoded into m bits. A sequence of digital pulses will therefore result in a sequence of these m bits signals. This sequence is predetermined and is known to the wrist unit 14. A certain bit sequence can precede the identification portion with the encoded digital signal to facilitate synchronization of the transmitter and receiver. FIG. 3A shows a typical format of the encoded digital signal transmitted from the chest unit 12 to the wrist unit 14 where the signal is comprised of a 3 bit synchronization part, an 8 bit identification part and a two bit data part. FIG. 3B shows a sequence of four digital pulses represented by a code having two bits per pulse, i.e., m=2. In this sequence, the first encoded group 00 represents the first digital pulse, the second encoded group 01 represents the second digital pulse, the third encoded group 11 represents the third digital pulse, and the next encoded group 10 represents the fourth digital pulse. This pattern, and its order, will be used each time the ECG signal is sampled and encoded. The pattern and its order will be changed if m is changed.

In operation, it is possible that a transmission error can occur. Sometimes these errors are only transient, in which case the last display reading will be maintained. It can also be the situation that the errors continue to occur due to interference from some outside source (such as an adjacent heartbeat monitor) where the errors are, for example, missing bits during repeated transmissions. Since the wrist unit 14 knows the predetermined code for the data portion of the signal, the missing of up to $2^m-1$ continuous signals will be immediately noticed and the missing signals can be accounted for. If too many signals ($>2^m-1$) are missing and therefore the interference is not a transient one, the frequency of the transmitter and receiver will be changed automatically. This can also be done on demand by the user. Thus, encoding of the digital pulse train 20 to include an identification part and a data part enables the receiving unit to accept only those signals sent from the associated chest unit and to detect and correct errors in the data part corresponding to the person's heartbeat. Details of how this occurs will be explained with respect to the apparatus of FIG. 4 (chest unit) and FIG. 5 (wrist unit).

Heartbeat Monitor Technique

This section will describe in general terms the technique of the present invention in which heartbeat monitoring is achieved in an advantageous manner. In a first step, a person's ECG signal is detected and then sufficiently amplified. This amplified signal is transformed into a digital pulse signal which can be used to initiate the wireless transmission of an encoded digital signal from the chest unit 12 to the wrist unit 14. The digital signal being transmitted includes an identification part and a data part as illustrated in FIG. 3A. The transmitted encoded data signal is received by a complementary receiver in wrist unit 14 and transformed therein back into the encoded digital signal. The resulting digital signal is separated into its identification part and its data part. Wrist unit 14 verifies the identification sequence to determine that the received signal is from the proper chest unit. If not, the signal is not accepted. If the identification step is satisfied, the data portion of the received signal is then checked to see whether it has the expected value. If the expected value is present in the received signal, then the display portion of the wrist unit is updated. Some or all of the data can also be stored in a memory contained in the wrist unit. As an option, the data can be first sent to the memory prior to being displayed.

The data portion of the transmitted encoded signal can represent a full heartbeat rate, or just a portion of it. For example, the number of ECG pulses in a 3-second interval can be represented. If this number is multiplied by 20, the approximate heartbeat rate in beats per minute will be known. This calculation can be done in the receiver unit or in the transmitter unit if the full heartbeat rate is to be transmitted to the receiver.

If the full heartbeat rate is transmitted, then less transmissions will be needed. In turn, this means that there will be less likelihood of interference from other sources and less power will be consumed. Of course, the number of transmissions in a given time from the transmitter to the receiver can be determined as a design parameter in accordance with considerations such as power, likelihood of interference, clocking requirements, etc. Various coding schemes are well known for selecting the number of ECG pulses to sample and the sampling repetition rate. In the practice of this invention, any of these known coding schemes, or a different one, can be chosen.

If the sequence of bits forming the data portion of the received signal is not maintained in the expected sequence, an error has occurred and the number of missing digital pulses is determined. These missing digital pulses are assumed to be evenly distributed in a corresponding time range and the display will be updated and/or the data will be stored in memory together with some annotation about the error.

In this embodiment, the occurrence of a certain number of errors ($>2^m-1$) within a given time frame means that the indicated heart beat rate will be unreliable. This will result in an automatically generated request for a frequency switch that is initiated in the wrist unit 14. This request for a change in transmission frequency can be blocked by the user or can be initiated on demand by the user. For example, the user may see that he or she will be in the presence of others using heartbeat monitor devices or maybe near exercise or other types of equipment which would interfere with the signal being transmitted from the chest unit. Known that such an interference may occur and may extend for a period of time, the user may wish to change the transmission frequency in order to avoid problems. Alternatively the user may recognize that any interference will be only transient, and therefore may wish to block a frequency change. In actual use, most persons would allow the monitor to automatically adjust. The amount of errors that will trigger a frequency change is a parameter that can be varied, according to the logic incorporated in the monitor.

If a change in transmission frequency is needed, a digital signal (frequency change signal) will be sent via wireless transmission from the wrist unit to the chest unit. This digital signal can include an identification part and a data part which specifies the new transmission frequency. The identification part of this digital signal allows the chest unit to know that the frequency change signal has been sent from the associated wrist unit and is therefore a correct command to change frequency. At the same time, the wrist unit changes the frequency of the receiver in this unit to match the new transmitter frequency of the chest unit 12. The transmission path from the wrist unit 14 to the chest unit 12, commanding a new transmission frequency, is not often used. However, once it is used the probability of a correct transmission must be high. For these reasons, it is preferable that there be only one possible transmission frequency for this path and that this transmission frequency be different from the frequencies used on the main transmission path, i.e., the transmission frequencies normally used to transmit the encoded digital signals from the chest unit to the wrist unit 14. As a further measure to increase the reliability of the second transmission path from the wrist unit 14 to the chest unit 12, the power of the frequency change signal from the wrist unit to the chest unit is higher than the power normally used for the transmission of encoded digital signals from the chest unit 12 to the wrist unit 14. This ensures that the necessary frequency change in the main transmission path will be made.

The following description will detail the components comprising the chest unit 12 and the wrist unit 14, which together comprise the heartbeat monitor 10.

Chest Unit (FIG. 4)

FIG. 4 shows the various components of chest unit 12 which are used to detect an ECG signal, amplify that signal and digitize it, encode it into an identification portion and a data portion, and then to wirelessly transmit it to wrist unit 14. The chest unit also includes means for receiving a frequency change signal from the wrist unit that will trigger a change in transmission frequency of the outgoing signals.

In more detail, chest unit 12 is typically carried on the breast of the target person such that this person's ECG signal 18 can be received by the input electrode terminals 24. These terminals 24 can be a part of the chest unit or the chest unit can be designed so that any sensor for detecting a biomedical response can be plugged into it. The ECG signal 18 is then amplified in a differential amplifier 26, producing the amplified signal represented by arrow 28. Amplified signal 28 is transformed into a digital pulse train 20 (FIG. 2) in the comparator 30, which has hysteresis. This hysteresis feature prevents the generation of more than one digital pulse from one heartbeat, due to outside disturbances of any type. The correlation between the ECG signal 18 and the digital pulse signal 20 was described with respect to FIG. 2.

The digital pulse signal 20 is sent directly to the transmitter 37 via line 32, and is also sent to an encoder means 34 via interconnection line 36. The rising flank of a digital pulse will trigger transmitting means 37 to wirelessly transmit an encoded electromagnetic signal 16 to a receiving means in the wrist unit 14. The rising flank of a digital pulse also triggers encoder 34 to provide the synchronization part, the identification part and the data part of the encoded digital signal represented by arrow 38 which is transmitted by the transmitting means 37. The digital pulse on line 32 is used only as a clock or timing pulse. Line 32 can be eliminated in an alternative design wherein clocking is internal in transmitter 37 or is provided by a portion of the encoded signal from encoder 34.

Encoded digital signal 38 is shown in FIG. 3A while a sequence of signals corresponding to the encoded data portion is shown in FIG. 3B. Every digital pulse in pulse train 20 (FIG. 2) results in advancing one step in the cycle of the encoded data signals. Therefore, FIG.

3B illustrates a pulse sequence corresponding to four digital pulses in the pulse train 20. Only a small and predetermined number of encoded signals must be transmitted by transmitting means 37.

Chest unit 12 also contains a receiver 40 and a comparator 42, termed a signal evaluator. Units 40 and 42 are used to receive a frequency change signal from wrist unit 14 indicating that a transmission frequency change is required, and to thereby provide a signal to the transmitter 37 to achieve this. In more detail, if errors beyond a given bound are noted in the data portion of the incoming digital signals in the wrist unit 14, a transmitted frequency change signal 17 will be wirelessly sent to chest unit 12 and is received by the receiver 40. This received signal contains the binary identification pattern unique to this heartbeat monitor and a data portion which will trigger a change in frequency. In this embodiment, chest unit 12 need not be equipped with error detection and correction means. It is only necessary that the data portion of the frequency change signal indicate that a new transmission frequency is desired. The data portion can also specify this new frequency or logic in signal evaluator 42 can specify the new frequency range over which the encoded digital signals will be sent.

The frequency change signal is sent to the comparator 42 (signal evaluator) which compares the coded identification pattern in the received digital signal with the coded identification pattern for this heartbeat monitor 10. As noted, this identification pattern is unique to this heartbeat monitor. If the comparison shows that the identification portion of the incoming signal matches that for this heartbeat monitor, comparator 42 will determine the new transmission frequency from the data portion of the received signal and will generate a digital frequency select signal 44 that is sent to the transmitter 37. As will be explained later, a signal evaluator in the wrist unit will provide a corresponding signal to the receiver therein in order that the reception and transmission frequencies will be matched.

Figure 5:
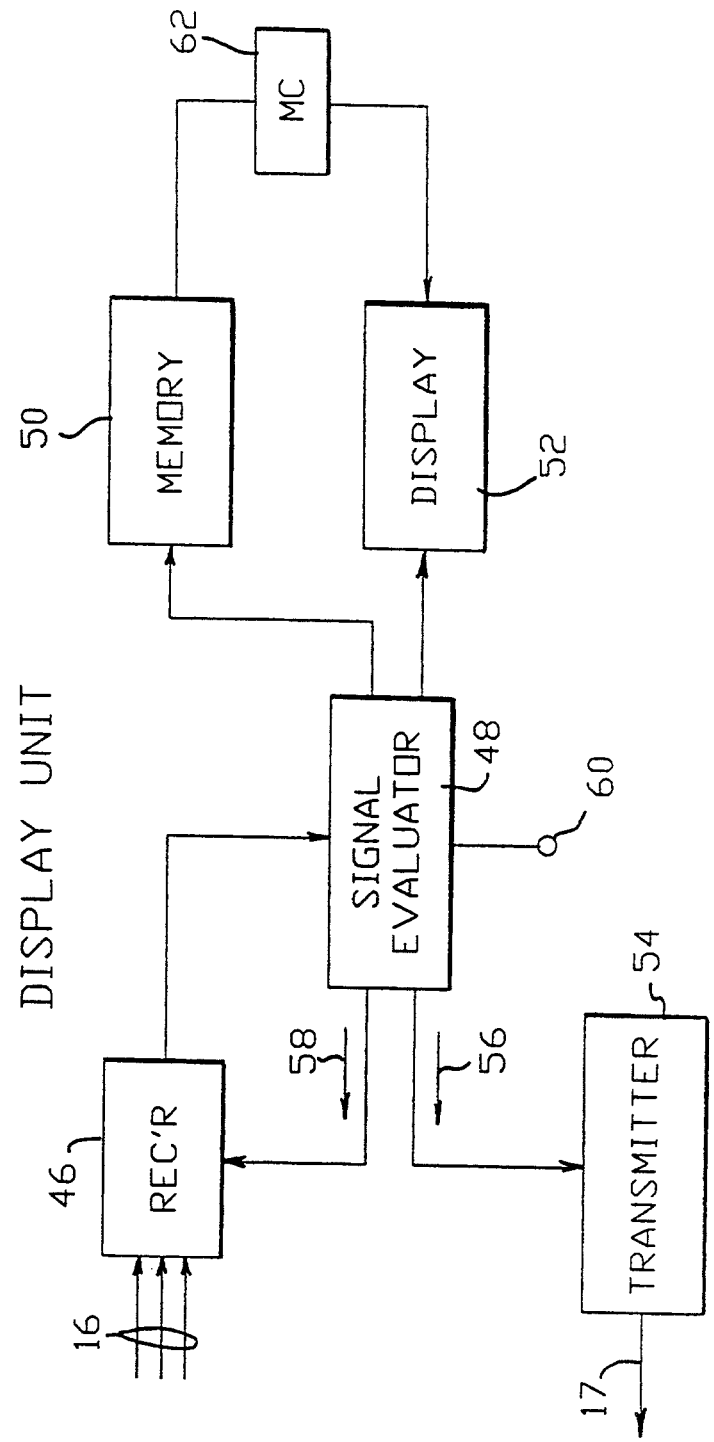
FIG. 5 is a schematic illustration of the wrist unit in more detail, showing the components comprising this unit.

Wrist Unit 14 (FIG. 5)

FIG. 5 illustrates the components which make up the wrist unit 14 (display). This unit provides the general functions of receiving the encoded digital signal representing a person's heartbeat, comparing the identification portion of the encoded signal to the appropriate reference identification pattern, and displaying and/or storing the data representing this heartbeat. Another function that is accomplished is a check of the data portion of the encoded signal to determine if any errors therein are within an acceptable bound or, if they are not, generating a signal to change the transmitter frequency as well as the frequency of the receiver in the wrist unit. As noted, this error detection and correction means takes into account transient errors which do not repeat and for which a frequency change is not required, as well as persistent errors which necessitate a change in transmission frequency in order to provide accurate data transmission.

In more detail, wrist unit 14 contains a receiver 46 for receiving the encoded digital signals 16 from chest unit 12, a comparator or signal evaluator 48 for analyzing the received encoded signals, a memory unit 50 in which data representing heartbeat can be stored, a display unit 52 for displaying to the user his or her heartbeat, and a transmitter 54 for the wireless transmission of frequency change signals to the chest unit in order to change the frequency of transmission.

The electromagnetic signal 16 is received by receiver 46 and transformed into a digital signal that is sent to the comparator 48. This digital signal is identical to the outgoing digital signal transmitted from chest unit 12 to wrist unit 14. In the comparator 48, the received digital signal is separated into its identification part and its data part. The identification part of the signal is compared to the preset and unit-specific identification unique to this heartbeat monitor. If the identification part of the incoming signal does not match the reference identification part, the incoming signal is ignored. If there is a match, comparator 42 then checks whether the data portion of the incoming signal is in the proper pattern order shown for example, in FIG. 3B for a situation in which m=2. If the data bit sequence matches the reference sequence, then the transmission from the chest unit 12 to the wrist unit 14 was error free and the necessary signal evaluation can be done. This means that the information can be sent directly to display 52 and/or stored in memory 50.

If the data portion is not the expected pattern, the number of missing patterns is determined. This number also gives information about the severity of the transmission error. The necessary approximations to compensate for this error are then done in the signal evaluation unit 48 in order to compensate for the error. For example, if only one bit is missing from the expected pattern, the signal evaluator would have built-in logic that would provide the bit so that the heartbeat rate corresponding to that data pattern would be displayed. If the error is a major one but does not repeat itself, the signal evaluator will cause the last displayed heartbeat rate to remain displayed.

If the occurrence of transmission errors is beyond a given bound then the signal evaluator unit will automatically generate a frequency change signal 56. This signal will be sent to the transmitter 54 for wireless transmission (represented by arrow 17) to the receiving means 40 in chest unit 12 (FIG. 4). The selection of the new transmission frequency takes into account the recent history of transmission failures for the various frequencies. This can be done by a table look-up feature in signal evaluator 48 where the number of transmission errors is stored for each of the transmission frequencies. Signal evaluator 48 also provides a frequency change signal 58 to the receiver 46. This enables receiver 46 to have a receiving frequency matching that of the new frequency used in the transmitter 37 (FIG. 4).

As an alternative, the user can use input terminal 60, which is connected to the signal evaluator 48, in order to either block the change of frequency or to initiate a change in frequency.

Normally a change(s) in transmission frequency will provide accurate data to the receiving unit. However, if the monitor detects errors that continue to occur after several frequency changes, the internal logic in the monitor will prevent the further display of heartbeat rate (blank screen), and/or will provide an alarm signal. In this way, the user is not fooled by the display of an inaccurate heartbeat as occurs with presently available monitors.

The data evaluation leading to information for updating the display can be sent to the memory 50 besides being entered into the display 52. Later this stored data can be displayed in the display 52. Microprocessor 62 would control the flow of heartbeat data from memory 50 to display 52. Display 52 can be of the visual type such as an LCD display and/or can be audible, as for example an alarm or other sound representing a heartbeat count.

The transmitter-receiver pair 37-46 can communicate on several frequencies and uses a relatively low power signal in order to preserve battery life. The transmitter-receiver pair 54-40 communicates on only one frequency and uses a relatively high power signal, in a preferred embodiment. This takes into account that the transmitter-receiver pair 37-46 is in constant use and that hardware is provided for error detection and correction. In contrast, the transmitter-receiver pair 54-40 is only rarely used and the monitor 10 has no error detection/correction facility with respect to the encoded signal representing a frequency change selection.

The transmitter 54 will continue transmitting an electromagnetic signal 17 until a correct electromagnetic signal 16 is delivered by transmitter 37 to receiver 46 in the wrist unit. If for some reason this synchronization fails, the user can synchronize the chest and wrist units by external means.

Figure 6:
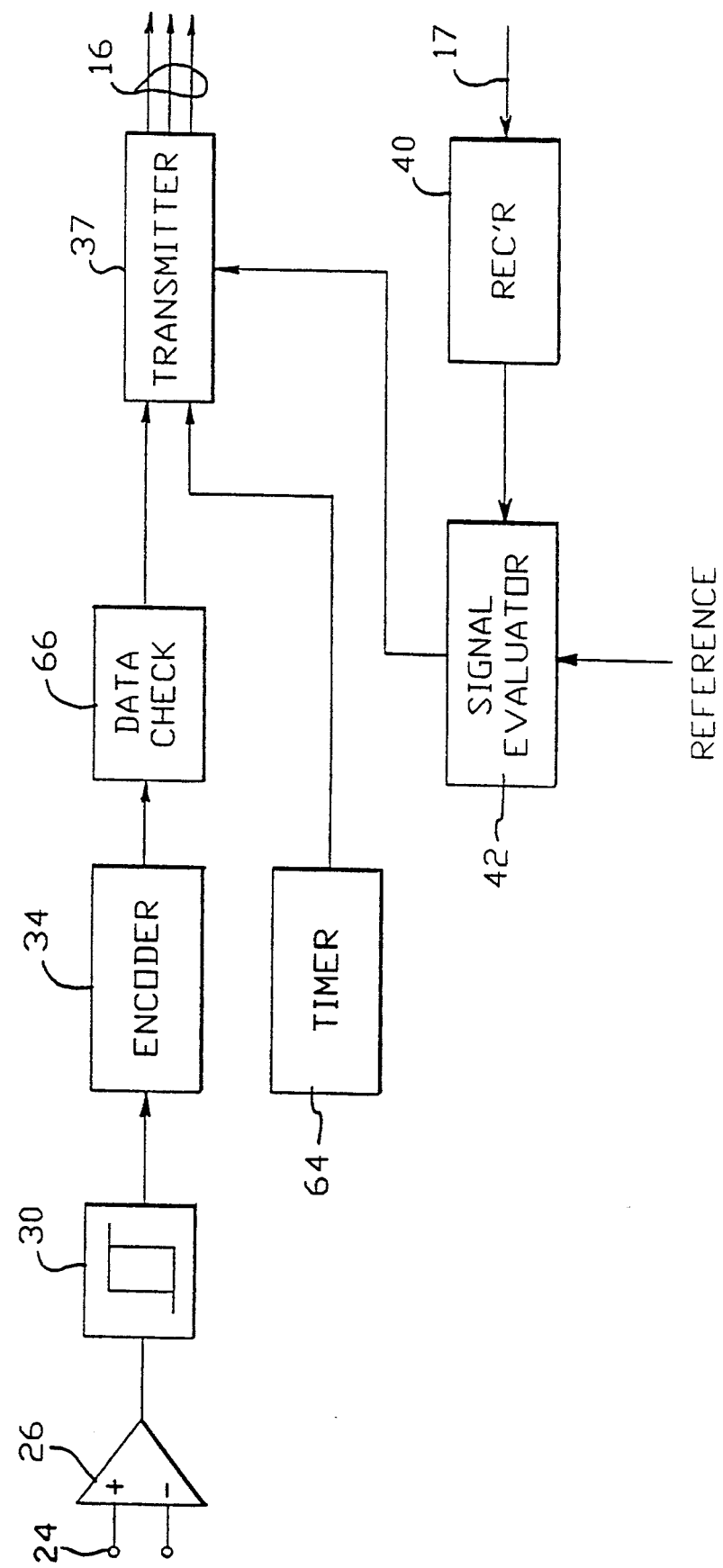
FIG. 6 is a schematic illustration of a modified chest unit, where the encoded digital signal represents the full heartbeat rate.

FIG. 6 illustrates a modification of the transmitter unit which is particularly adapted for wireless transmission of the full heartbeat rate. The same reference numerals will be used in this figure as were used in FIG. 4, for components having the same or similar functions. Of course, the unit of FIG. 4 can also be used to encode and transmit the full heartbeat rate.

In more detail, the transmitter of FIG. 6 includes the amplifier 26, comparator 30, encoder 34, transmitter 37, receiver 40 and signal evaluator 42 shown also in FIG. 4. However, a timer 64 is now used to trigger the transmitter 37 for wireless transmission of the encoded digital signal from encoder 34. In this embodiment, a data check circuit 66 is used to enable error detection and correction of the encoded digital signal prior to its being transmitted to the receiver unit. For example, this can be done by use of a parity bit. This helps to ensure accuracy if the entire heartbeat rate is to be transmitted, particularly if the heartbeat rate is not transmitted at a high repetition frequency, i.e., if there is a long time duration between each wireless transmission of heartbeat rate. The receiver unit of FIG. 5 can be used to receive and evaluate the full heartbeat rate sent by the transmitting unit.

Figure 7:
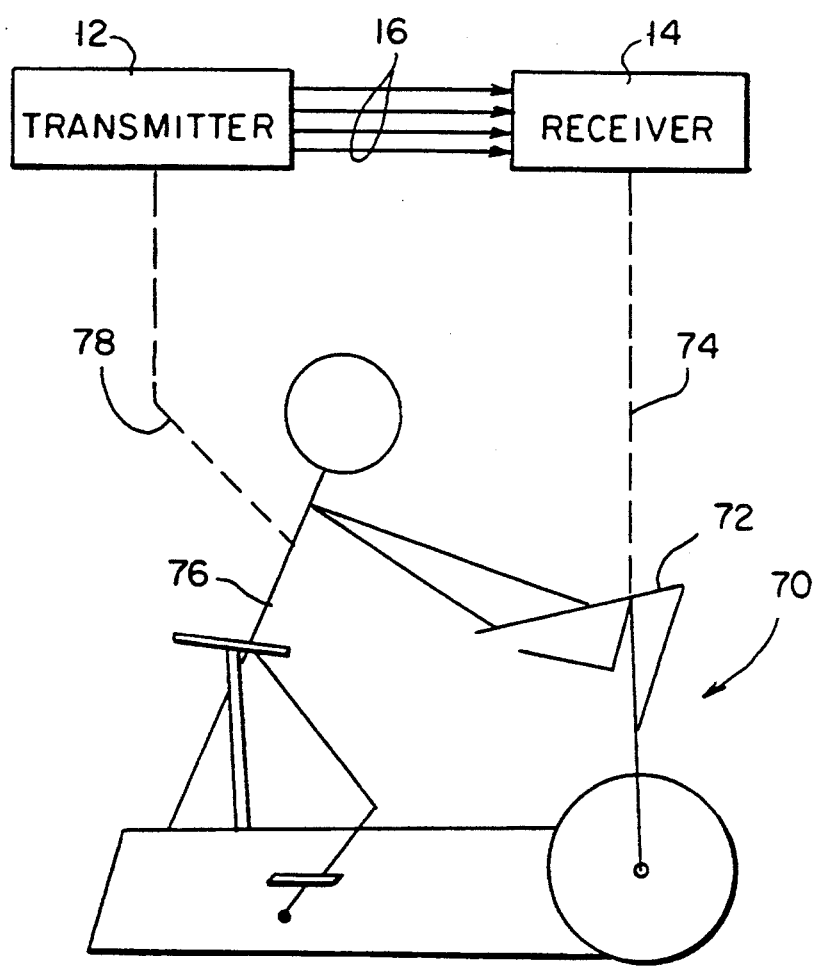
FIG. 7 is a schematic illustration of a person on exercise equipment, where the transmitter portion of the monitor is worn by the person and the receiver portion of the monitor is mounted on the exercise equipment.

FIG. 7 schematically illustrates a piece of exercise equipment 70 (for example, an exercise bike) having a handle-bar portion 72 on which the receiver 14 is located, as indicated by the dashed line 74. A person 76 sitting on the exercise bike 70 is wearing the transmitter unit 12, as indicated by the dashed line 78. Wireless transmission, indicated by the arrows 16, occurs between the transmitter 12 and the receiver 14. During exercise the person's heart rate will vary and will be recorded on the display unit in receiver 14, for easy viewing by the person since the display unit is clearly visible on the handle-bar portion 72 of the exercise bike.

While the invention has been described with respect to particular embodiments thereof, it will be apparent to those of skill in the art that variations can be made therein without departing from the spirit and scope of the present invention. For example, many different types of encoding can be used to represent the identification and data portions of the transmitted signals. Also, the rate of sampling of the ECG pulses can be varied, as can the repetition rate at which wireless transmissions of the encoded digital signal are made. The frequency change signal used to trigger a new transmission frequency can be transmitted over a multiple frequencies range rather than over a single selected frequency. The frequency ranges used in the main transmission path can be chosen by the designer in accordance with known principles of wireless transmission, which in personal use monitors is of a short range.

As noted, the principles of digitization of the transmitted heartbeat signal, transmission frequency changes, and signal encoding to ensure the accuracy of the communicated results are used to provide personal use monitors far superior to those presently being marketed. However, such principles may be applied to other than personal use monitors. It is recognized, though, that the provision of such features is unique in a wearable heartbeat monitor where the monitor includes a wearable transmitting unit and an associated display unit. These features are also unique to monitors where the display (receiver) unit is located on exercise equipment or is a small unit that can be placed in a suitable location for viewing by the user. Such units are distinguishable from large hospital units wherein a central computer is used to coordinate a multiplicity of transmitting and/or display units.

While the monitor has been illustrated in an embodiment thereof for monitoring heartbeat rate, it will be understood by those of skill in the art that a signal indicative of another physical condition can be monitored. For example, an acoustical sensor can detect a pulse or a thermometer sensor can detect a temperature. This type of monitor can be applied to measure and display any type of life function, in persons or animals. Additionally, wireless monitors for measuring physical conditions other than life functions can utilize the principles of error detection and correction described herein.

I claim:

1. A method for monitoring the heartbeat of a person, comprising the following steps:
    obtaining an ECG signal of heartbeat pulses from said person,
    amplifying said signal,
    digitizing and encoding said amplified signal to produce an encoded digital signal, said encoding of said signal providing a portion for identification purposes and a data portion representing the occurrence of pulses s in said ECG signal,
    wirelessly transmitting said encoded digital signal to a display unit,
    comparing said transmitting encoded signal with a reference signal to determine if there is a match to the identification portion of said transmitted signal,
    comparing the data portion of said transmitted signal with a reference signal to see if there is a match therebetween, and transmitting pulses representing said heartbeat to a display viewable by said person if both the identification portion and the data portion of the received encoded digital signal successfully match a reference signal,
    rejecting said transmitted encoded digital signal if there is no match of the identification portion of said transmitted signal, and
    changing the frequency of transmission of said encoded digital signal if mismatches in excess of a given number occur when the data portion of said encoded digital signal is compared with the data portion of the reference signal where said changing of frequency reduces the number of said mismatches.

2. The method of claim 1, include the step of changing the frequency over which said encoded digital signals are transmitted in response to the receipt of a frequency change signal from said display unit, said frequency change signal being wirelessly transmitted from said display unit.

3. The method of claim 2, including the further step of storing selected information representing said heartbeat in a memory in said display unit for later display of said selected information.

4. The method of claim 3 including the step of binary encoding said amplifier signal.

5. A method for heartbeat monitoring of a person utilizing a transmitter unit which transmits a person's ECG signal to a receiver unit for display to the person of his or her heartbeat including the steps of:
digitizing said ECG signal and encoding it to provide an encoded digital signal having a first part corresponding to identification information and a second part corresponding to said person's heartbeat,
wirelessly transmitting said encoded digital signal to said receiver unit,
receiving said encoded digital signal in said receiver unit,
comparing said encoded digital signal with a reference signal to determine if the identification information of said received encoded digital signal matches a reference signal and discarding the received signal if no such match is made,
comparing the data portion of said received signal to a reference signal to determine the accuracy of heartbeat data contained in the received encoded digital signal,
changing the frequency over which wireless transmission occurs if errors exist in the data portion of the received encoded digital signal representing the person's heartbeat, said changing of frequency reducing the number of said errors and
displaying the person's heartbeat.

6. A heartbeat monitor, including:
a wearable transmitting means for producing an encoded digital signal representative of a person's heartbeat, said transmitting means including sensor means for producing an electrical signal representative of a person's heartbeat, said transmitter means containing a transmitter for wireless transmission of said encoded digital signal to a display means and
a display means for producing a display of said person's heartbeat, said display means including a receiver for receiving said wireless transmission of said encoded digital signal, means for determining if said received encoded signal is from said transmitting unit, means for detecting errors in the received encoded digital signal and means for correcting said errors in said wireless transmission.

7. The monitor of claim 6, where said means for correcting errors includes means for changing the frequency over which said encoded digital signal is transmitted in response to a frequency change signal produced by said display means, said frequency changing reducing the likelihood of errors in said wireless transmission.

8. The monitor of claim 6, where said transmitting means includes means for encoding said electrical signal representative of a person's heartbeat to produce said encoded digital signal, said signal including a first part identifying said monitor and a second part which represents the heartbeat of said person.

9. The monitor of claim 8, wherein said means for determining includes means for comparing said received encoded digital signal with a reference signal produced by said display means to determine if said received encoded digital signal has been sent from said transmitting means.

10. The monitor of claim 9, where said means for detecting errors includes means for comparing said received encoded digital signal with a reference signal to determine if said received encoded digital signal has a data part matching the data part of said encoded digital signal transmitted by said transmitting means.

11. A monitor for measuring and displaying a human body condition, comprising:
a transmitter unit capable of being worn by a person to be monitored, said transmitter unit including:
sensor means for detecting a first signal indicative of said human body condition,
means for digitizing said first signal to produce a digital signal representative of said first signal,
encoder means for encoding said digital signal to produce an encoded digital signal, said encoder means including means for producing an identification part unique to said monitor and means for producing a data part representing said human body condition,
transmitting means for transmitting said encoded digital signal via wireless transmission over a selected frequency to a display unit,
a display unit for displaying information received by said display unit, said displayed information being indicative of said human body condition, said display unit including:
receiver means for receiving said encoded digital signal via wireless transmission from said transmitter means,
comparator means for determining if said received encoded digital signal is from said transmitter unit,
comparator means for determining if said data part of said received encoded digital signal matches a predetermined reference pattern produced by said display unit, or if there is a mismatch therebetween,
means for producing a frequency change signal which causes a change in said selected frequency of wireless transmission if said mismatch exists, and
a display means for displaying to said person information representative of said human body response.

12. The monitor of claim 11, where said monitor measures the heartbeat of said person, said display unit including means for removably securing attaching it to a person's body.

13. The monitor of claim 11, where said monitor measures the heartbeat of said person, said display unit further including a transmitter means for wirelessly transmitting said frequency change signal to said transmitter unit, said transmitter unit including means for determining if said frequency change signal is from said display unit.

14. The monitor of claim 13, where said means for producing said frequency change signal produces an encoded digital signal having information therein identifying a new selected frequency.

15. The portable monitor of claim 13, where said means for determining if said frequency change signal is from said display unit includes a receiver for receiving said frequency change signal and a comparator for comparing information in said frequency change signal to a reference signal produced by said transmitter unit to determine if there is a match, and means to provide a signal to said transmitting means in said transmitter unit to change said selected frequency if said match is found.

16. A heartbeat monitor, comprising:

a transmitting means for producing an encoded digital signal representative of a person's heartbeat, said transmitting means including a transmitter for wireless transmission over a frequency range of said encoded digital signal to a receiving means in a display means, encoding means for producing said encoded digital signal, said encoded digital signal having a first part identifying said transmitting means and a second part representative of a person's heartbeat, a display means for displaying information representing the person's heartbeat, a receiving means for receiving said encoded digital signal sent via wireless transmission from said transmitting means, means for determining if said received encoded digital signal is from said transmitting means, and frequency change means for changing the frequency over which said encoded digital signal is transmitted from said transmitter if errors occur in the data portion of said encoded digital signal received by said receiving means.

17. The heartbeat monitor of claim 16 where said display means include memory means for storing data representative of said heartbeat, for later display to said person.

18. The heartbeat monitor of claim 16, further including means for allowing said person to change the frequency range over which said encoded digital signal is transmitted from said transmitting unit to said display unit.

19. The heartbeat monitor of claim 16, where said frequency change means includes means for wirelessly transmitting a digital frequency change signal from said display means to said transmitting means and further means for producing information in said frequency change signal identifying the display unit from which it is sent.

20. The heartbeat monitor of claim 19, where said frequency change means includes means for producing information in said frequency change signal describing a selected frequency over which said encoded digital signals are to be wirelessly transmitted.

21. A method for heartbeat monitoring of a person using a transmitter means which transmits data representing a person's ECG signal to a receiver means for display of the person's heartbeat, including the steps of:

digitizing and encoding said ECG signal in said transmitter means to produce an encoded digital signal having a first part corresponding to identification information associating said encoded digital signal with said transmitter means and a second part corresponding to data representing a person's heartbeat rate, wirelessly transmitting over a first frequency said encoded digital signal to said receiver means reading said identification information in the received encoded digital signal to determine if it is from said transmitter means, rejecting said received encoded digital signal if it is not from said transmitter means, reading the data portion of a received encoded digital signal determined to be from said transmitter means to determine said person's heartbeat rate, detecting minor errors in the data portion of said received encoded digital signal, correcting said minor errors in the data portion of said received encoded digital signal, and displaying said heartbeat rate.

22. The method of claim 21, further including the step of changing said frequency over which said encoded digital signal is transmitted from said transmitter means to said receiver means if errors exist in the data portion of said received encoded digital signal.

23. The method of claim 22, including the steps of wirelessly transmitting a frequency change signal from said receiver means to said transmitter means to trigger said change of frequency of transmission.

24. The method of claim 23, including the step of producing an identification portion in said frequency change signal which identifies said receiver means.

25. The method of claim 24, including the step of producing a frequency data portion of said frequency change signal which specifies a new frequency over which said wireless transmission will occur.

26. The method of claim 21, including the further step of storing in memory data corresponding to said person's heartbeat, for later display.

27. A method for monitoring a human body condition comprising the steps of:

sensing said condition using a sensor located in the area of the body where said condition occurs, producing an electrical signal representative of said condition, digitizing said electrical signal to produce a digital signal, encoding said digital signal to produce an encoded digital signal representative of said human body condition, wirelessly transmitting said encoded data signal over a first transmission frequency, receiving said encoded digital signal, reading said received encoded digital signal to determine if there is an error therein, producing a frequency change signal if said error is found, changing the transmission frequency to a second value in response to said frequency change signal, and displaying said human body condition to said person.

28. The method of claim 27, including the step of producing an identification portion in said encoded data signal, said identification portion being read in said reading step.

29. The method of claim 28, including the step of producing a data portion representing said human body condition in said encoded data signal.

30. The method of claim 27, including the step of storing said received encoded digital signal.

31. The method of claim 27, where said sensing step senses said person's heartbeat.

32. A heartbeat monitor, comprising in combination a transmitting means for producing an encoded digital signal representative of a person's heartbeat, said transmitting means including a transmitter for wirelessly transmitting said encoded digital signal over a first frequency to a display means, a display means including a receiver for receiving said encoded digital signal, error detection means for detecting an error in the signal received by said receiver, decoding means for decoding said encoded digital signal received by said receiver, a display for displaying said person's heartbeat, and frequency change means for automatically changing said first frequency over which said encoded digital signal is transmitted if said error is detected.

33. The monitor of claim 32, where said frequency change means includes means for wirelessly transmitting a frequency change signal from said display means to said transmitting means when said specified error is determined.

34. The monitor of claim 33, further including means for enabling said transmitting means to know that said frequency change signal is from said display means.

35. The monitor of claim 34, where said frequency change means includes further means for selecting the frequency over which said encoded digital signal is wirelessly transmitted.

36. The monitor of claim 32, further including means for correcting errors in the received encoded digital signal, without an automatic change of frequency.

37. A monitor for measuring and displaying a biomedical condition including:

a transmitting means including encoding means for producing an encoded digital signal representative of said biomedical condition, said transmitting means including a transmitter for wirelessly transmitting said encoded digital signal to a receiver over a first frequency, a receiver for receiving said encoded digital signal, a display means for displaying said biomedical condition, detection means for detecting errors in said received encoded digital signal, and correction means for automatically changing said transmitter and said receiver to provide accurate wireless transmission therebetween.

38. The monitor of claim 37, where said correction means includes frequency change means for changing said first frequency over which said encoded digital signal is wirelessly transmitted.

39. The monitor of claim 38, where said correction means includes means for producing a frequency change signal, means for wirelessly transmitting said frequency change signal to said transmitting means, and means for encoding said frequency change signal to produce a portion thereof which identifies its source.

40. The monitor of claim 37, including identification means for determining that the encoded digital signal received by said receiver is from said transmitter.

41. The monitor of claim 37, where said transmitting unit produces an encoded digital signal representation of a heartbeat.

42. The monitor of claim 41, where said monitor includes means for electrically powering it by a battery.

43. The monitor of claim 37, where said transmitting means and said display means include means for removably securing said transmitting means and said display means to said person.

44. The monitor of claim 37, where said monitor includes means for electrically powering said monitor by a battery.

45. The monitor of claim 37, further including an exercise means for enabling a person to exercise, said display means being located on said exercise means for direct viewing by said person.

* * * * *